United States Patent
Liu et al.

(10) Patent No.: US 10,576,426 B2
(45) Date of Patent: Mar. 3, 2020

(54) PLASMA SEPARATOR APPARATUS AND ASSOCIATED METHODS

(71) Applicant: THE TRUSTEES OF THE UNIVERSITY OF PENNSYLVANIA, Philadelphia, PA (US)

(72) Inventors: Changchun Liu, Bala Cynwyd, PA (US); Haim H. Bau, Swarthmore, PA (US); Michael G. Mauk, Greenville, DE (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 448 days.

(21) Appl. No.: 15/105,887

(22) PCT Filed: Dec. 18, 2014

(86) PCT No.: PCT/US2014/071099
§ 371 (c)(1),
(2) Date: Jun. 17, 2016

(87) PCT Pub. No.: WO2015/095491
PCT Pub. Date: Jun. 25, 2015

(65) Prior Publication Data
US 2016/0310904 A1  Oct. 27, 2016

Related U.S. Application Data (60) Provisional application No. 62/091,085, filed on Dec. 12, 2014, provisional application No. 61/918,425, filed on Dec. 19, 2013.

(51) Int. Cl.
*B01D 63/08* (2006.01)
*B01D 69/06* (2006.01)
(Continued)

(52) U.S. Cl.
CPC ........ *B01D 63/087* (2013.01); *A61M 1/3496* (2013.01); *B01D 61/147* (2013.01);
(Continued)

(58) Field of Classification Search
CPC .............. A61M 1/3496; A61M 1/3472; A61M 1/3486; A61M 1/3693; A61M 1/3695;
(Continued)

(56) References Cited

U.S. PATENT DOCUMENTS 4,963,325 A   10/1990 Lennon et al.
5,169,789 A   12/1992 Bernstein
(Continued)

FOREIGN PATENT DOCUMENTS

AU   2009/218752 B2   9/2009
EP        0336483 A1  10/1989
(Continued)

OTHER PUBLICATIONS

Balu et al., "Patterning of superhydrophobic paper to control the mobility of micro-liter drops from two-dimensional lab-on-paper applications", Lab on a Chip, Jan. 1, 2009, vol. 9, No. 21, p. 3066.
(Continued)

*Primary Examiner* — John Kim
(74) *Attorney, Agent, or Firm* — BakerHostetler (57) ABSTRACT

A plasma separator includes a vertical chamber with a membrane or membranes partially or fully covering the internal chamber walls and forming an inner cavity to accommodate whole blood. The plasma separator further includes a plasma collection space separated from the inner cavity with one or more membranes and a plasma removal port.

22 Claims, 5 Drawing Sheets

(51) Int. Cl.
*B01D 61/14* (2006.01)
*G01N 33/49* (2006.01)
*A61M 1/34* (2006.01)

(52) U.S. Cl.
CPC .............. *B01D 63/08* (2013.01); *B01D 69/06* (2013.01); *G01N 33/491* (2013.01); *A61M 2202/0415* (2013.01); *A61M 2205/70* (2013.01); *B01D 2313/58* (2013.01)

(58) Field of Classification Search
CPC ...... A61M 2202/0415; A61M 2205/70; B01D 2313/58; B01D 39/2017; B01D 61/147; B01D 63/08; B01D 63/087; B01D 69/06; G01N 33/491
See application file for complete search history.

(56) References Cited

U.S. PATENT DOCUMENTS

| | | |
|---|---|---|
| 5,254,248 A | 10/1993 | Nakamura |
| 6,106,732 A | 8/2000 | Johnston et al. |
| 8,691,592 B2 | 4/2014 | Chen et al. |
| 8,697,007 B2 | 4/2014 | Bau et al. |
| 8,911,938 B2 | 12/2014 | Mauk et al. |
| 9,233,368 B2 | 1/2016 | Bau et al. |
| 2008/0280285 A1 | 11/2008 | Chen et al. |
| 2010/0112723 A1 | 5/2010 | Battrell et al. |
| 2012/0024788 A1 | 2/2012 | Kelso |
| 2012/0245042 A1 | 9/2012 | Liu et al. |
| 2013/0112612 A1 | 5/2013 | Blankenstein et al. |
| 2013/0164779 A1 | 6/2013 | Kelley et al. |
| 2013/0209331 A1 | 8/2013 | Rodenfels et al. |

FOREIGN PATENT DOCUMENTS

| | | |
|---|---|---|
| EP | 2413138 A2 | 2/2012 |
| WO | WO 2006/122311 A2 | 11/2006 |
| WO | WO 2008/076395 A2 | 6/2008 |
| WO | WO 2008/130463 A2 | 10/2008 |
| WO | 2009/109997 A1 | 9/2009 |
| WO | WO 2013/103360 A1 | 7/2013 |

OTHER PUBLICATIONS

Liu et al., "Membrane-based, sedimentation-assisted plasma separator for point-of-care applications", Analytical Chemistry, Oct. 5, 2013, vol. 85, pp. 10463, 10465-10467.

PLASMA SEPARATOR APPARATUS AND ASSOCIATED METHODS

CROSS-REFERENCE TO RELATED APPLICATIONS

This application is a National Stage Application filed under 35 U.S.C. 371 of International Application No. PCT/US2014/071099, filed Dec. 18, 2014, which claims the benefit of and priority to U.S. Provisional Application No. 61/918,425 dated Dec. 19, 2013 and U.S. Provisional Application No. 62/091,085 dated Dec. 12, 2014 the contents of each of which are incorporated herein in their entireties.

GOVERNMENT RIGHTS

The invention was made with government support under grant number AI099160 awarded by the National Institutes of Health. The government has certain rights in the invention.

TECHNICAL FIELD

The present disclosure relates to the field of diagnostic devices and to the field of blood plasma purification.

BACKGROUND

Often, high-sensitivity, point-of-care (POC) clinical tests, such as HIV viral load, require large volumes of plasma. Although centrifuges are ubiquitously used in clinical laboratories to separate plasma from whole blood, centrifugation is generally inappropriate for on-site testing. Suitable alternatives are not readily available to separate the relatively large volumes of plasma from milliliters of blood that may be needed to meet stringent limit-of-detection specifications for low-abundance target molecules. The present disclosure provides, inter alia, a simple-to-use, low-cost, pump-free, membrane-based, sedimentation-assisted plasma separator capable of separating a relatively large volume of plasma from undiluted whole blood within minutes. In one embodiment, this plasma separator includes of an asymmetric, porous, polysulfone membrane housed in a disposable chamber. The separation process takes advantage of both gravitational sedimentation of blood cells and size exclusion-based filtration. An exemplary plasma separator demonstrated a "blood in—plasma out" capability, consistently extracting 275±33.5 µL, of plasma from 1.8 mL of undiluted whole blood within less than 7 min. The device was used to separate plasma laden with HIV viruses from HIV virus-spiked whole blood with recovery efficiencies of 95.5% ±3.5%, 88.0% ±9.5%, and 81.5% ±12.1% for viral loads of 35 000, 3500, and 350 copies/mL, respectively. The separation process is self-terminating to prevent excessive hemolysis. The HIV-laden plasma was then injected into a exemplary microfluidic chip for nucleic acid testing and was successfully subjected to reverse-transcriptase loop-mediated isothermal amplification (RTLAMP), demonstrating that the plasma is sufficiently pure to support high-efficiency nucleic acid amplification.

Over two-thirds of the estimated 34 million people living with HIV/AIDS worldwide reside in developing countries, and nearly three-fourths of the 2.5 million new HIV infections in 2011 occurred in these countries. HIV viral load testing plays a critical role in clinical decisions on when and whether to switch to second-line treatment; in optimizing the duration of first-line treatment by detecting occult nonadherence; in diagnosing HIV infection in babies under 18 months of age, born to HIV-infected mothers, in whom the presence of HIV antibodies is not indicative of the disease; and in detecting early newly infected individuals during the seroconversion window period when antibodies are present at undetectable concentrations. Although a standard practice in developed countries, HIV viral load determination is not widely used in low- and middle-income countries, because of technical constraints, lack of testing facilities, lack of trained personnel, and cost. There is an urgent need to develop an affordable, simple, easy-to-use point-of-care (POC) diagnosis technology for HIV viral load testing in resource-constrained settings.

Usually, plasma separation from raw whole blood is required for HIV viral load testing, as the presence of blood cells and components in the sample, such as hemoglobin and lactoferrin, may inhibit DNA polymerase and lead to low amplification efficiency, inaccurate quantification, and even amplification failure. In addition, prevailing HIV viral load standards are based on the number of virus copies in a unit volume of plasma—not whole blood. In clinical laboratories, plasma separation is typically carried out with a benchtop centrifuge. Separation of relatively large volumes of plasma from whole blood remains a challenge in resource-constrained settings, because of the lack of laboratory infrastructure.

Various microfluidic approaches have been developed to separate plasma from whole blood at the point of care. Such approaches, however, work with small (<100 microliter) volumes of blood and plasma that are insufficient for conventional nucleic acid-based molecular diagnostics such as PCR.

To overcome the shortcomings of the above devices, some have used a centrifugation approach that requires a high-speed spinner and electrical power, which may not be readily available in resource limited settings. Others have used filtration-based separation, but existing separation-based methods require extensive dilution that adversely affects the limit-of-detection, and the limit-of-detection is critical in viral load detection.

SUMMARY

This disclosure provides simple-to-manufacture, simple-to-use, disposable, pump-free, membrane-based, sedimentation assisted, plasma separation devices for large-volume, rapid plasma extraction from raw, whole blood. In addition to the membrane-based filtration, the disclosed separator takes advantage of gravitational sedimentation of blood cells to reduce membrane clogging and to enable the extraction of relatively large plasma volumes directly with a pipet without a pump and/or excessive wash. The separator provides "blood in-plasma out" process for preparing samples for nucleic acid-based testing. We demonstrated extraction of 275±33.5 µL plasma from 1.8 mL undiluted whole blood in 7 min. The utility of this membrane-based, sedimentation-assisted, plasma separator for diagnostics was tested by separating plasma containing HIV virus from whole blood spiked with HIV. The HIV-laden plasma was then inserted into a microfluidic chip that carried out nucleic acid extraction and amplification, demonstrating that the virus was retained in the plasma, potential polymerase inhibitors were successfully removed, and the plasma had sufficient purity for polymerase activity. The plasma separator described herein can be used as a stand-alone module to separate plasma from whole blood. In this mode of operation, the device is suitable for use for onsite testing in resource-poor regions of the world, where funds, trained personnel, and laboratory facilities are in short supply and in settings lacking electrical power. While one motivation for developing the plasma separator described herein is HIV viral load testing, the disclosed separators are useful in various critical applications and are not necessarily limited to plasma isolation or HIV testing. For example, separating plasma to detect presence of antigens and antibodies, and various proteins in blood analysis such as cell-free nucleic acids (cfNAs), protein biomarkers, and other bloodborne pathogens such as Hepatitis A (HAV), Hepatitis B (HBV), Hepatitis C (HCV) and Parvovirus B 19 (B 19V), and syphilis. Additionally, other applications of nucleic acid tests utilizing plasma could also benefit from the disclosed plasma separator. For example, such a device may be used for circulating nucleic acids in plasma including nucleic acid sequences from tumors, traumatized tissue, short DNA fragments from cancerous tissue, fetal DNA and RNA, tumor-associated viral RNA, and markers associated with stroke and myocardial infarction. Without being bound to any particular theory, the disclosed technology uses a non-horizontal membrane to perform filtration/separation of a fluid sample. As material (e.g., cells, particulates) in the fluid sample sediments at the base of the membrane, a portion of the membrane remains un-blocked by the sedimented material and remains available to perform efficient filtration of the medium in which the sedimenting material resides.

A plasma separator includes a vertical chamber with a membrane or membranes partially or fully covering the internal chamber walls and forming an inner cavity to accommodate whole blood. The plasma separator further includes a plasma collection space separated from the inner cavity with one or more membranes and a plasma removal port. The chamber optionally further comprises the inner walls are patterned and the space among the features forms part of the plasma collection space. The pattern may be a pillar array and/or comprise of vertical grooves. The chamber may features support for the membrane. The chamber may have a circular cross-section, rectangular cross-section, ellipsoidal cross-section or triangular cross-section. The chamber may have a cross-section varying in dimensions along its height.

In one embodiment, a plasma separator includes a frame elongate along a central longitudinal axis, the frame having a top end and a bottom end spaced from the top end along the longitudinal axis, the frame defining a void elongate along the central longitudinal axis, a collection conduit, and a collection trench transverse to the central longitudinal axis and in fluid communication with the collection conduit. The frame further defines an outlet at a top end of the collection conduit. The plasma separator also includes a pair of membranes disposed parallel to one another within the void, the pair of membranes together defining an inlet space to the void, the inlet space being defined between the pair or membranes.

The present disclosure also provides methods of separating a component from a fluid (e.g., plasma), the methods suitably including, e.g., disposing blood between a pair of membranes. The pair of membranes is supported by a frame that defines a void elongate along a central longitudinal axis in which the pair of membranes are disposed, a collection conduit parallel to the central longitudinal axis, and a collection trench transverse to the central longitudinal axis and in fluid communication with the collection conduit. The frame further defines an outlet at a top end of the collection conduit. The method may also include, through the outlet, collecting plasma that has passed through one of the pair of membranes, into the collection trench and the collection conduit.

In another embodiment, a separator may include a frame defining a void and a conduit defining an outlet andat least one membrane disposed within the void and supported by the frame, the at least one membrane at least partially defining an inlet.

DETAILED DESCRIPTION OF ILLUSTRATIVE EMBODIMENTS

Figure 1:
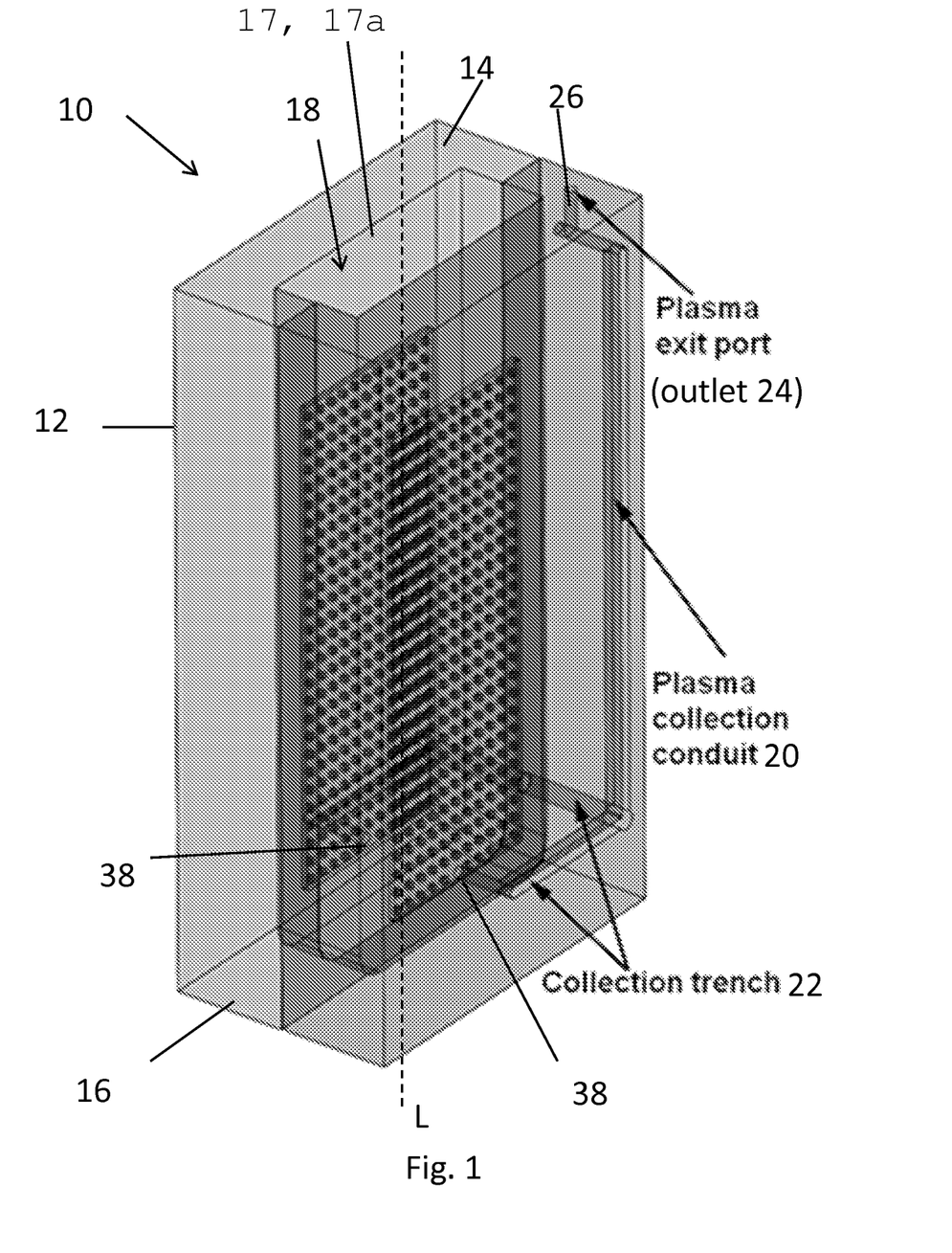
FIG. 1 shows a perspective view of one embodiment of a plasma separator.
Figure 2:
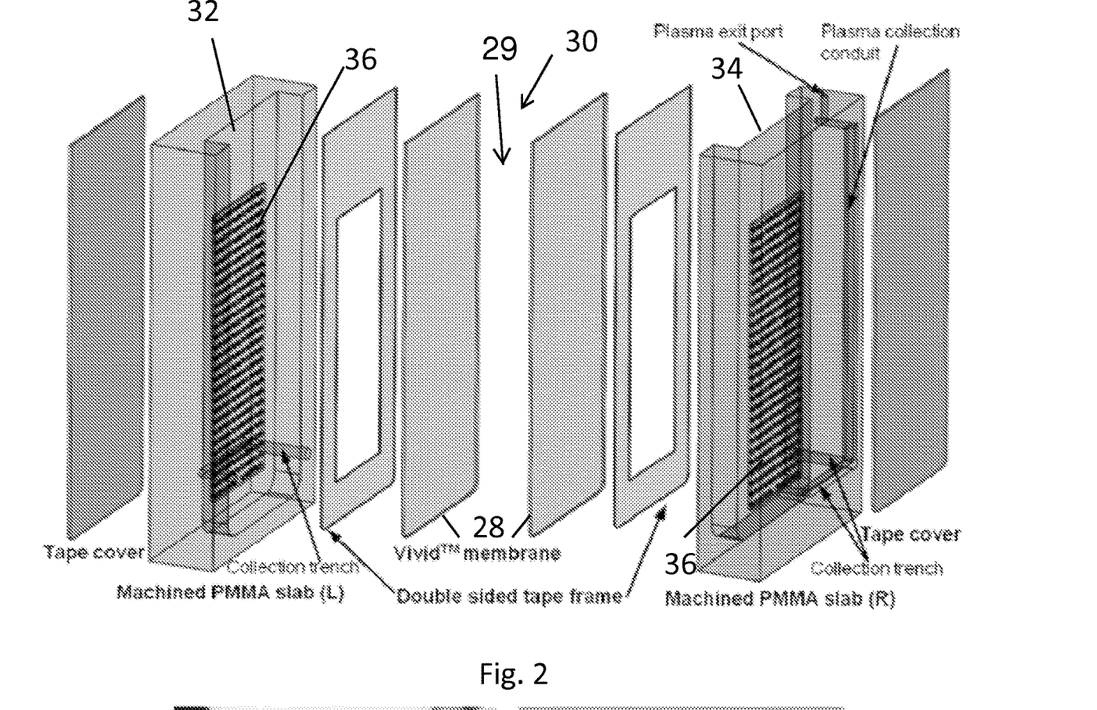
FIG. 2 shows an exploded perspective view of the plasma separator shown in FIG. 1.

With reference to FIGS. 1 and 2, a plasma separator 10 includes a frame 12 elongate along a central longitudinal axis L, the frame having a top end 14 and a bottom end 16 spaced from the top end along the longitudinal axis, the frame defining a chamber 17 that further defines a void 18 elongate along the central longitudinal axis L the chamber having one or more inner walls 17a, a collection conduit 20 that is elongate along an axis parallel to the central longitudinal axis L, and a collection trench 22 transverse to the central longitudinal axis L and in fluid communication with the collection conduit 20. The frame 12 further defines an outlet 24, such as a plasma removal port, at a top end 26 of the collection conduit 20. The plasma separator also includes at least one membrane 28 disposed within the void 18. The at least one membrane 28 may include two membranes 28 or a single folded membrane. The membrane/s 28 may be disposed such that two layers are parallel or approximately parallel to each other. For example, one or both of the layers may be 1, 2, or 5 degrees offset relative to axis L. The at least one membrane 28 together define an inner cavity 29 and an inlet space 30 to the inner cavity 29 within the void 18, the inlet space being defined between the membrane or pair or membranes. The void is partially defined by a left side 32 of the frame 12 and a right side 34 opposite the left side 32. Left side 32 and right side 34 may be disposed between /1 mm and 1 cm apart depending on the volume of the whole blood that the device will separate. For example, left side 32 and right side 34 may be disposed approximately 5 cm apart. The frame 12 optionally further comprises a plurality of projections 36 (e.g., micropillars, ridges, and the like) that extend from the left and right sides 32, 34 of the frame towards the pair of membranes 28. Each of the left and right sides 32, 34 may also define an aperture 38 in fluid communication with the collection trench 22. Either or both of the at least one membrane 28 and inner cavity 29 (or a portion thereof) may have hydrophilic surfaces. Alternatively, either or both of the at least one membrane 28 and inner cavity 29 (or a portion thereof) may have superhydrophobic surfaces. Superhydrophobic surfaces can reduce the non-specific absorption of analytes such as the HIV virus.

Figure 5:
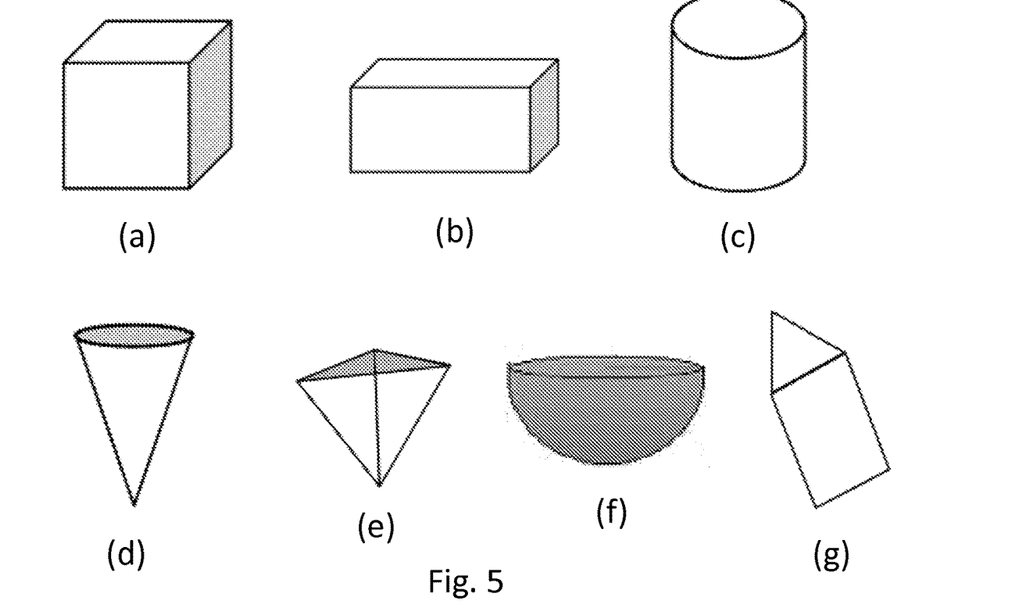
FIGS. 5a-g show various embodiments of chamber and/or membrane shapes that may be employed with a plasma separator.

While the pair of membranes 28 disclosed in FIGS. 1 and 2 are shown generally parallel to each other and spaced apart, in alternative embodiments, a membrane or membranes formed into different shapes may be used. For example, as shown in FIG. 5, at least one membrane may be formed into a cube (a), a cuboid (b), a cylinder (c), a cone (d), a pyramid (e), a partial sphere (f), or a prism (g).

Figure 3:
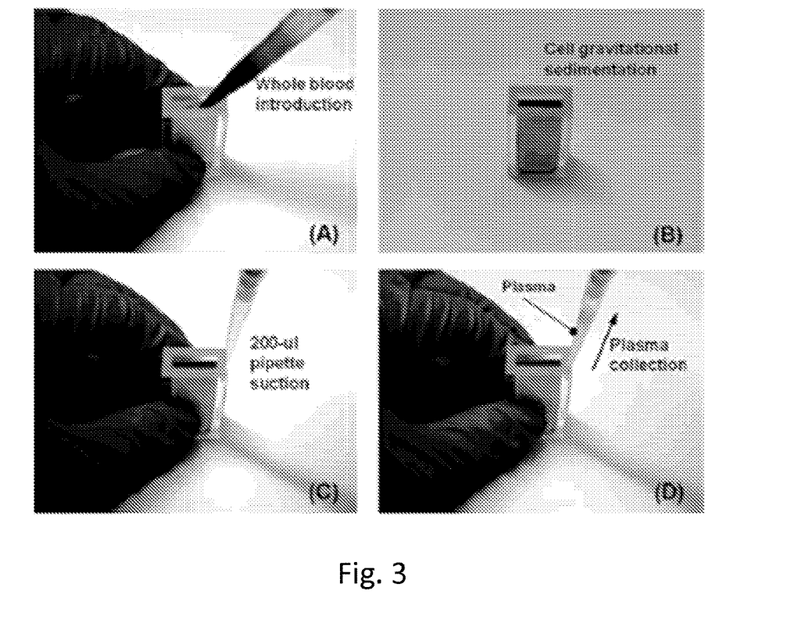
FIG. 3 shows a process by which a plasma separator is used to collect plasma from whole blood.

With reference to FIG. 3, a method of separating plasma includes disposing whole blood between the pair of membranes 28 that are supported by frame 12 as described above. After plasma passes through the membranes 28, into collection trench 22, and collection conduit 20, plasma is collected through outlet 24.

Additionally, the plasma separator 10 may be monolithically integrated and fluidically coupled to a NA chip that integrates the steps of lysis, nucleic acid extraction, enzymatic amplification, and detection, as described in International Application No. PCT/US2006/018534 (filed May 11, 2006); U.S. application Ser. No. 11/937,975 (filed Nov. 9, 2007); U.S. application Ser. No. 13/398,192 (filed Feb. 16, 2012); U.S. application Ser. No. 13/477,332 (filed May 22, 2012); International Application No. PCT/US2007/025699 (filed Dec. 14, 2007); International Application No. PCT/US2008/001554 (filed Feb. 4, 2008); U.S. application Ser. No. 12/331,483 (filed Dec. 10, 2008); U.S. application Ser. No. 12/331,508 (filed Dec. 10, 2008); U.S. application Ser. No. 12/515,616 (filed Aug. 23, 2010); U.S. application Ser. No. 12/535,718 (filed Aug. 5, 2009); and PCT/US2012/025196 (filed Feb. 15, 2012), each or which is hereby incorporated by reference in its entirety herein.

Additional Disclosure

In an exemplary embodiment, a plasma separator included a 21 mm wide×11 mm thick ×40 mm tall poly (methyl methacrylate) (PMMA) chamber whose wide side walls are covered with plasma separation membranes (see FIG. 2). The plasma separator chamber was comprised of two bonded, machined PMMA compartments (items L and R in FIG. 2). Each PMMA compartment was machined from a 5.5 mm (0.216 in.) thick PMMA slab, although other materials (polymers, metals, and the like) may be used. A 38 mm tall×15 mm wide×2.5 mm deep depression was milled into each of the slabs with a precision, computer numerical control (CNC) milling machine (HAAS Automation, Inc.). It should be understood that the depression described here is illustrative only, as a depression may have a cross-sectional dimension in the range of from about 1 to about 10, about 100, or even about 1000 mm. It should also be understood that the slabs need not have identical depressions. An array of micropillars, each 300 μm long, 300 μm wide, and 100 μm deep, with a pitch of 800 μm was milled into the floor of the depression. Alternatively, the pillar array can be hot-embossed. The micropillar array served as a support for the plasma separation membrane.

The space outside the pillars was connected to a 500 μL wide and 200 μm deep horizontal plasma collection trench located at the bottom of the PMMA compartment. The bottom of the pillar array region connected to the collection trench with a 500-μm-diameter, vertical vias. The collection trench was covered with transparent tape (Polyvinyl Films, Inc., Sutton, Mass.). The main plasma collection conduit was machined at the back of the right compartment (see FIGS. 1 and 2). At its top, the plasma collection conduit terminated with a 1.0-mm-diameter exit port. The size of the exit port was designed to match tightly the outer diameter of a 200 μL pipet tip that is used to collect the plasma. The bottom of the plasma collection conduit was connected to the collection trench.

An asymmetric polysulfone membrane (Vivid GR, Pall Life Sciences, East Hills, NY) was cut to a length of 38 mm and a width of 15 mm with a $CO_2$ laser (Universal Laser Systems). A double-sided adhesive tape (McMaster—Carr, New Brunswick, N.J.) was cut with the laser to the same external dimensions as the membrane. A rectangular window 20 mm long ×10 mm wide (an area of 2 cm2) was then removed from the adhesive tape center to leave a rectangular frame. The adhesive frame was then attached to the plasma separation membrane. The resulting laminate was placed on top of the pillar array and pasted to the frame surrounding the pillar array to entirely cover the pillar array. The two PMMA compartments were then solvent-bonded with acetonitrile (Sigma—Aldrich) at room temperature to form the plasma separator. Other methods of securing the PMMA compartments include double-sided tape and a "kit" that includes several few frames and different kinds of membranes that are inserted into the frames, thus allowing the user to place blood from a single patient into several different separator devices. Different separators may be color-coded to indicate that one is for plasma, one is for red blood cells, and so on.

When the plasma separator's chamber was filled with blood, the separator allowed plasma to filter through the plasma separation membrane into the space among the pillars, drain to the bottom of the pillar array and into the collection trench. The exposed area of each membrane available for plasma filtration was ~2 $cm^2$, providing a total filtration area of ~4 $cm^2$.

Deidentified whole blood samples from healthy donors were collected by the Penn Center for AIDS Research (CFAR) with the approval of the Institutional Review Board (protocol: 814752) and stored in 10 mL Vacutainer (Becton-Dickinson) blood collection tubes containing ethylenediaminetetraacetic acid (EDTA) anticoagulant. All fresh blood samples were handled without any dilution. The blood samples were spiked with intact HIV-1 virus (AcroMetrix HIV-1 High Control, Benicia, Calif.) to concentrations of $3.5 \times 10^4$, $3.5 \times 10^3$, and $3.5 \times 10^2$ copies/mL.

The 1.8 mL volume of the EDTA anticoagulated whole blood spiked with the virus was manually loaded into the plasma separation chamber with a 1.0 mL pipet (FIG. 3(A)). The blood was left to sediment for 5 min. During this time interval, blood cells settled toward the bottom of the separation chamber (FIG. 3(B)). After 5 min at room temperature (20-25 C), the tip of a 200-μL Eppendorf pipet (Brinkman Instruments, Inc., Westbury, NY) was inserted into the plasma exit port, forming a seal between the pipet tube and the port (FIG. 3(C)). A negative pressure was then applied with a pipet. The plasma containing virus filtered through the Vivid plasma separation membrane while the red blood cells (RBCs) and white blood cells (WBCs) were retained in the chamber, since their sizes exceeded the membrane's pore size. Downstream of the plasma separation membrane, the plasma entered the pillar array region, and emptied into the main plasma collection conduit through the plasma collection trenches. The plasma from the main collection conduit was then collected by the pipet (FIG. 3(D)) and its volume was measured with the pipet.

The concentration of hemoglobin in the extracted plasma was quantified with relative units, using a sample of lysed whole blood as a reference. Relative hemoglobin concentrations were evaluated with a ND-1000 spectrophotometer (Nano-Drop Technologies, Wilmington, DE) as previously described. The separator's recovery efficiency for HIV virus was evaluated by comparing its performance with that of standard laboratory procedures. To establish a reference, anticoagulated whole blood samples containing intact HIV virus at various concentrations were centrifuged at full speed for 10 min with a benchtop centrifuge at room temperature (Labnet International Inc., Woodbridge, N.J.). Both HIV-laden plasma extracted with the plasma separator and centrifuged plasma were analyzed by standard quantitative PCR at the Molecular Pathology Laboratory (the Hospital of the University of Pennsylvania) to determine the viral load. The viral loads of the plasma separated with the device and that of the centrifuged plasma were then compared.

Figure 4:
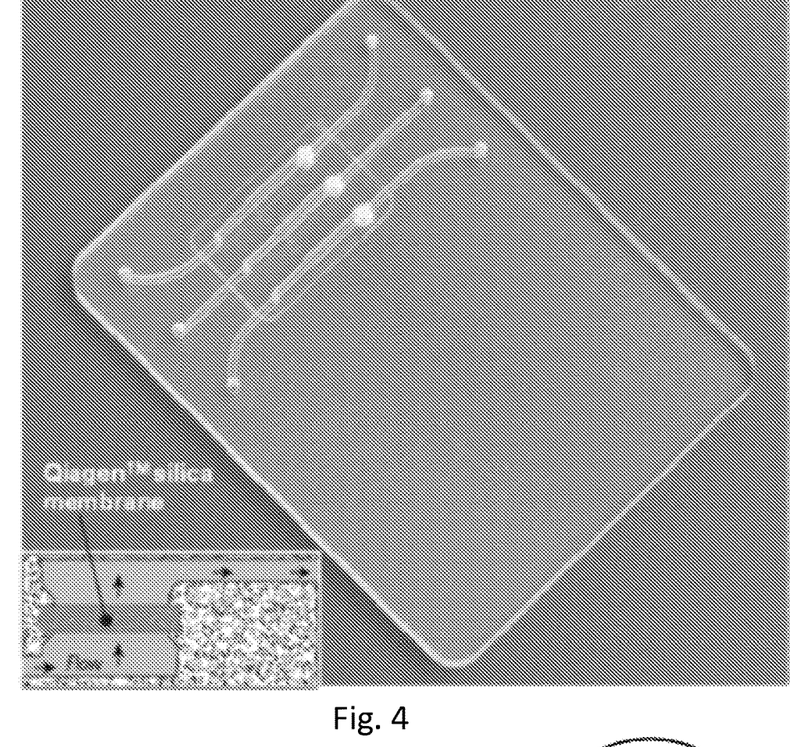
FIG. 4 is a top view of a microfluidic chip for nucleic acid testing with an inset that shows a schematic illustration of the flow-through operation for nucleic acid extraction.

Nucleic Acid Testing. The extracted plasma containing the HIV virus was subsequently amplified in our custom-made microfluidic chip (FIG. 4). The chip and its performance were previously described. Briefly, the chip contains three independent, multifunctional, 5.0 mm long, 1.0 /mm wide, 3.0 mm deep, and ~15.0 µL in volume amplification reactors. Each of these reactors is equipped with a flow-through Qiagen silica membrane (QIAamp Viral RNA Mini Kit) at its entry port. The 140 µL of plasma collected with our plasma separator was mixed with 560 µL of lysis buffer (QIAamp Viral RNA Mini Kit, Qiagen, Valencia, Calif.) and inserted into one of the amplification reactors. The nucleic acids bound to the Qiagen silica membrane in the presence of high chaotrophic salts (such as guanidinium chloride) and low pH.38 Subsequent to the sample introduction, 500 µL of Qiagen wash buffer 1 (AW1), containing chaotropic salt and ethanol, was pipetted into the chip to remove any remaining amplification inhibitors. Then, the silica membrane was washed with 500 µL of wash buffer 2 (AW2) containing 70% ethanol, followed by air drying for 30 s. Next, 22 µL of RT-LAMP master mixture, which contains all the reagents necessary for the RT-LAMP,36,39 0.5×EvaGreen@ fluorescence dye (Biotium, Hayward, Calif.), and 8 units of RNase inhibitor (Life Technologies), was injected into each reaction chamber through the inlet port. Subsequently, the inlet and outlet ports were sealed using transparent tape (Scotch brand cellophane tape, 3M, St. Paul, Minn.) to minimize evaporation during the amplification process. The nucleic acid chip was placed on a heater and heated to 63° C. for ~60 min. The fluorescence excitation and detection were carried out with a minute, portable ESE optical detection system (Qiagen ESE GmbH, Stockach, Germany).

Membranes provide a convenient and effective means to separate plasma from whole blood without a need for centrifugation. The 330-µm-thick Pall Vivid asymmetric polysulfone membrane has a mean pore size of ~100 µm on its upstream surface and ~2 µm on its downstream surface. The asymmetric structure of the membrane allows for a gentle capture of the cellular components without lysing them while providing sufficiently fine pores to prevent any passage of intact cells. The Pall GR Vivid plasma separation membrane was selected because, in contrast to glass fiber media, the Vivid membrane does not shear and lyse cells (which may lead to the contamination of the plasma) and it can handle higher whole blood volume per surface area (40-50 µL/cm$^2$) than other commercially available membranes, although the present disclosure is not limited to using Vivid membranes. Minimizing cell lysis is particularly important for the HIV viral load testing since clinical standards are based on viral load in plasma and exclude HIV cDNA that might be present in cells. The total working area of the membrane in the exemplary plasma separator is ~4.0 cm$^2$, although the working area in a device may be from about 0.01 cm$^2$ to about 1 cm$^2$, 10 cm$^2$, or even 50 cm$^2$.

In typical membrane-based plasma separators, the membrane is placed horizontally at the bottom of the sample introduction chamber. This arrangement, however, results in blood cells sedimenting directly onto the membrane. Although this arrangement may expose the membrane to spatially uniform cell concentration, the membrane eventually clogs. Such devices may be capable of extracting plasma from whole blood within ~10 min when subjected to a relatively strong negative pressure provided by a pressure pump, but this plasma volume is insufficient for applications involving low-abundance analytes. Under such operating conditions, to extract 275 µL of plasma, a membrane with an area of 72 cm$^2$ and a whole blood volume of 2.3 mL would be needed, and such a large membrane is disadvantageous for point of care devices. Without being bound to any particular theory of operations, the smaller area of the membranes in the disclosed devices also reduce nonspecific binding of target analytes. In addition, a relatively strong negative pressure operation is likely to result in substantial hemolysis, and also is incompatible with plasma separators that are intended to be an integral part of a point of care device.

In contrast, in the plasma separators the membrane is positioned vertically. The vertical configuration allows for gravitational sedimentation of blood cells in a direction that is parallel to the membrane surface rather than directly onto the membrane, as in existing designs. This arrangement reduces membrane blockage by blood cells and increases the membrane's ability to handle larger volumes of blood without excessive hemolysis. FIG. 3 illustrates the operation of the plasma separator. First, undiluted, fresh or anticoagulated whole blood was introduced into the plasma separator's chamber (FIG. 3(A)). The blood was left to sediment gravitationally for ~5 min (FIG. 3(B)). Since the blood cells are ~10% denser than the plasma in which they are suspended, the blood cells sink to the bottom of the chamber. At the conclusion of the 5-min sedimentation period, the fluid at the top of the chamber is much clearer than the fluid next to the bottom. After 5 min, a pipet was inserted into the plasma exit port (FIG. 3(C)). The good fit between the pipet tube and the collection conduit provides a hermetic seal. When a gentle negative pressure was applied to the pipet (FIG. 2(D)), the resulting pressure difference across the membrane induced plasma flow through the membrane while the blood cells were left behind. The micropillar array provided mechanical support for the separation membrane, preventing the membrane from deforming and compromising the separation between the blood and plasma sides of the membrane.

Without being bound to any particular theory, it is likely that most of the plasma that transfused through the membrane came from the upper layer of the separator's chamber, where the blood cells were most diluted, allowing the membrane to purify a much greater volume of plasma than it would have if it were horizontally positioned. The plasma collection self-terminates once the blood level drops beneath the level of the pillar array exposing the upstream side of the membrane to air. Self-termination may be achieved before the Vivid membrane clogs with cells, minimizing the risk of hemolysis. The exemplary devices were designed to separate up to 300 µL of plasma.

Figure 6:
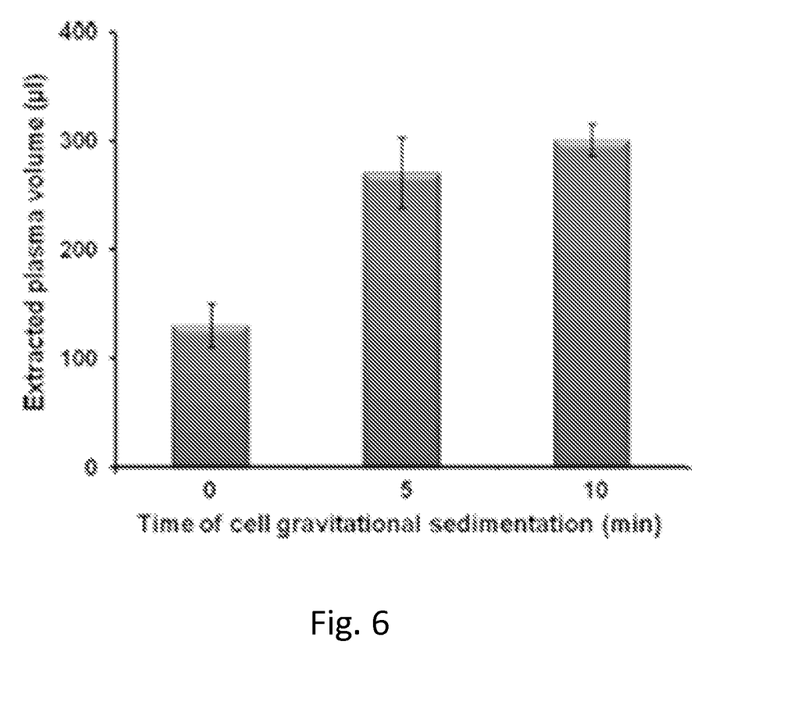
FIG. 6 shows the volume of the extracted plasma by a plasma separator as a function of the gravitational sedimentation time.

The optimal sedimentation time (Ts) for efficient plasma recovery was 5 min for some exemplary devices. FIG. 6 depicts the volume of the extracted plasma (µL) as a function of the sedimentation time (Ts, min). The error bars correspond to the scatter of the extracted plasma volume obtained in three different experiments. In the range of sedimentation intervals 0<Ts<5 min, as the sedimentation time increased, so did the extracted plasma volume. When the sedimentation time was 5 min, the volume of the extracted plasma was 275±33.5 µL, which is more than twice the volume (130±23.1 µL) extracted without any waiting period after the filling of the separator's chamber with whole blood. In the latter case, some sedimentation had still occurred during the filling of the chamber with whole blood. Increasing Ts beyond 5 min led to diminishing returns as 275 µL was close to the exemplary separator's maximum capacity of 300 µL, which is achieved at 5 min<Ts<10 min. At least 100 ul of plasma may be obtained to perform testing.

The disclosed plasma separators have several advantages over previously reported membrane-based plasma separation devices. First, the separator is capable of extracting a relatively large volume of plasma from whole blood without a need to dilute or wash the blood, which could be detrimental to the limits of detection when the target is present in low abundance, as typically is the case with HIV viral load in patients on antiretroviral therapy. Second, the plasma can be collected with a conventional 200-µL pipet without a need for an external vacuum pump. Third, by taking advantage of gravitational sedimentation, one can increase membrane capacity and reduce membrane pressure drop. As a result, the separation process can be driven by a relatively low (negative) pressure. Perhaps more significantly, the separation is carried out with a relatively modest size membrane, which reduces nonspecific binding of target analytes. Fourth, the separation process is self-terminating, preventing exertion of excessive forces on the cells and avoiding undesired cell breakage. Fifth, the plasma separator can operate without any specialized instrumentation and without electrical power.

Because high shear stresses can damage blood cells and lead to contamination of the plasma, the extent of hemolysis was determined in the membrane-based, sedimentation-assisted, plasma separator. Plasma was obtained using both the disclosed separators and benchtop centrifugation. The hemoglobin concentration in the plasma extracted with the disclosed devices was 3.5±1.2 mg/dL (n=3). The hemoglobin concentration in the plasma obtained by centrifugation of the same blood samples was 2.6±0.9 mg/dL (n=3). These concentrations are close to the reported hemoglobin concentration of ~2.4 mg/dL naturally present in human plasma. Furthermore, the hemoglobin concentration of 3.5 mg/dL in extracted plasma was far below the level that causes interference in most assays (500 mg/dL). Because hemolysis is a general measure of the damage to blood cells, the low levels of hemolysis in the plasma extracted with the exemplary device indicated that the device produced good-quality plasma.

Figure 7:
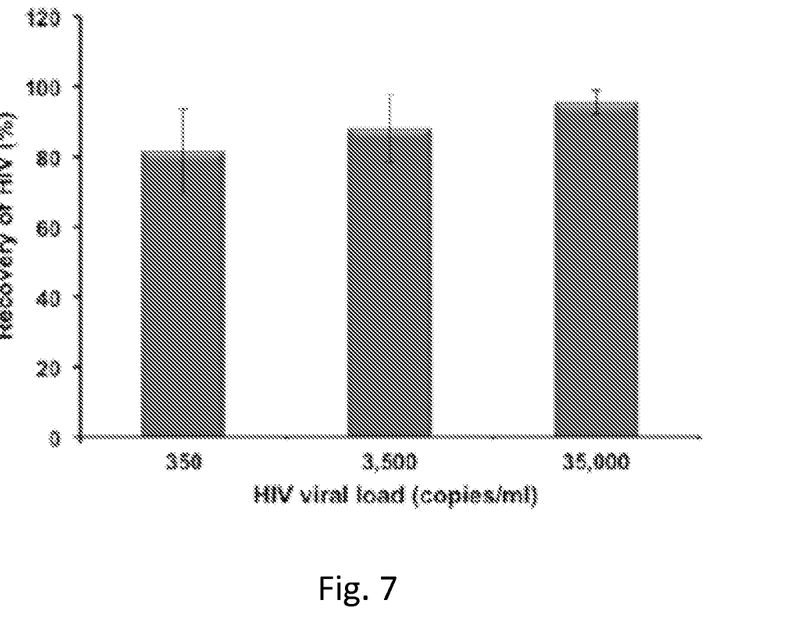
FIG. 7 shows recover efficiency of HIV virus of a plasma separator as a function of the whole blood viral load.

Since an objective in separating the plasma from the whole blood is to enable quantification of plasma viral load, it was also examined whether the disclosed separation process adversely affected the measured HIV-1 concentration in plasma. Loss of target can occur, for example, because of nonspecific binding to the separation membrane and the structural members of the separator such as the relatively high surface area pillar array. FIG. 7 depicts the recovery efficiency (RR) of HIV virus of our plasma separator as a function of the whole blood viral load (viral RNA copies/mL). One may define the recovery efficiency (RR) as the ratio of the number of virus copies ($C_{device}$) in the plasma separated with our custom-made plasma separator and the number of virus copies ($C_{centrifuge}$) in plasma obtained by centrifugation from the same blood sample.

$$RR(\%) = \frac{C_{device}}{C_{centrifuge}} \times 100$$

The error bars correspond to the scatter of three independent experiments. In all cases, the recovery rate was above 80%. As the HIV viral load in the whole blood increased, so did the recovery efficiency. At low viral load (3.5×102 copies/mL), the recovery efficiency was 81.5% ±12.1%. At high viral load (3.5×104 copies/mL), the recovery efficiency reached 95.5% ±3.5%. The reason for the increase in the recovery efficiency with higher viral loads is not known. Recovery efficiency smaller than 100% may, perhaps, resulted from nonspecific binding of viruses to the membrane and the plasma separator's structure. As the number of virus particles increases, the nonspecific binding sites may saturate diminishing the fraction of viruses lost. Conceivably, the recovery rate can be even further increased by appropriate surface treatments and the use of sacrificial additives to saturate potential binding sites.

To test the suitability of the plasma extracted with the disclosed separators for POC, nucleic acid-based detection, we spiked plasma separated with our device with HIV virus, and carried out the amplification process in the custom-made, microfluidic chip, which chip integrates a nucleic acid separation membrane within the amplification reactor and using the bound nucleic acids as templates in the amplification process. As a result, the nucleic acid purification process in the chip is less stringent than in a traditional PCR process, where the separation and purification processes take place outside the reaction chamber. Thus, the chip provides a demanding test ground for the evaluation of the "quality" of the separated plasma. For amplification, we use the RT-LAMP process as it is efficient, robust, and can be carried out at a constant temperature (60-65° C.). Other work has successfully used our chip for mosquito genotyping and to detect HIV virus in raw (unprocessed) saliva with a limit of detection of less than 10 viral particles in a sample.

Figure 8:
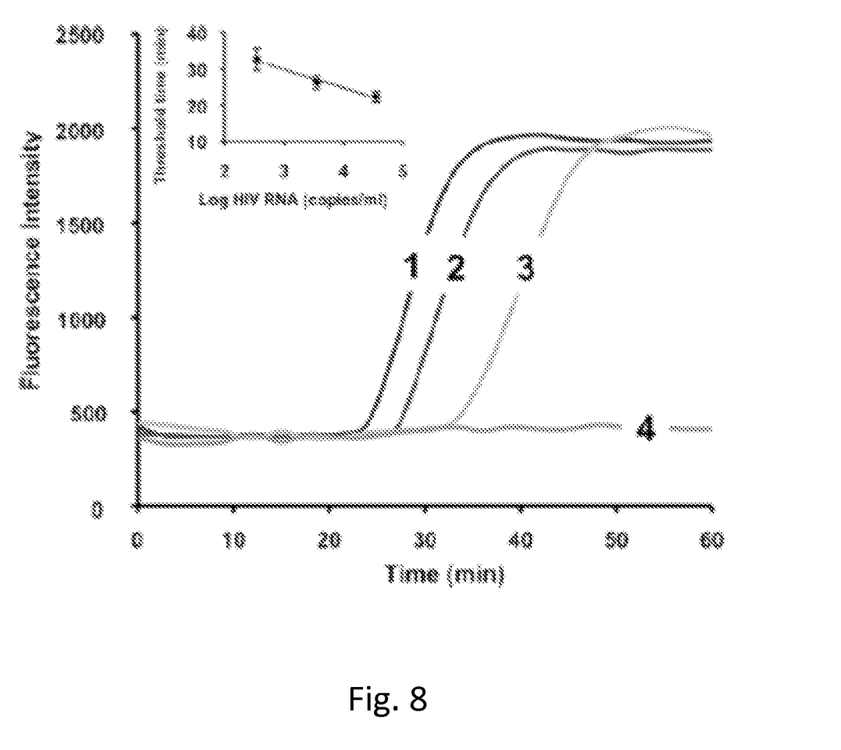
FIG. 8 illustrates real-time monitoring of RT-LAMP amplification of plasma samples extracted with the plasma separator and spiked with $3.5 \times 10^4$ (curve 1) $3.5 \times 103$ (curve 2), $3.5 \times 102$ (curve 3), and 0 (curve 4) (negative control) viral RNA copies per mL with an inset showing threshold time Tt (in minutes), as a function of the HIV concentration (expressed in terms of viral RNA copies per mL) (n-3).

The plasma separator described herein extends the use of the chips to detecting and quantifying HIV in blood samples. The amplification process was monitored, in real time, by tracking the fluorescence emission intensity of intercalating dye. FIG. 8 depicts the real-time fluorescence intensity as a function of time when the extracted plasma sample contained 3.5×104, 3.5×103, 3.5×102, and 0 (negative control) HIV viral RNA copies per mL. The fluorescence intensity of the negative control (no target) remained nearly constant throughout the entire detection period (60 min), indicating negligible amplicon production. The threshold time (Tt) is defined as the reaction time that elapses until the fluorescent signal increases above a predetermined baseline level. FIG. 8 (inset) depicts the threshold time Tt (min) as a function of the RNA concentration (C) on a semilogarithmic plot. In the range of 350<C<35 000 viral RNA copies per mL, the threshold time Tt decreases nearly linearly as a function of log C. The data correlates well with the formula Tt=45.1-5.1 log(C), where Tt is expressed in minutes ($R2=0.98$). The experiment indicates that the plasma separated with the plasma separator is suitable for nucleic acid amplification, and that a simple threshold time measurement could be used for target quantification. Because the optical detector used in this work can monitor only one reactor at a time, the reactors were operated sequentially. One may also use a CCD camera-based detector to facilitate concurrent imaging of an array of reactors and parallel detection of targets at various dilutions and/or multiple targets.

In sum, presented here is a low-cost, disposable, easy-to-use, pump-free, large-volume, stand-alone, sedimentation-assisted, plasma separator for rapid extraction of plasma from undiluted, whole blood. The separator does not require any electrical power. Unique to the device is the combined use of two separation principles: cell sedimentation and size-based filtration. The plasma can be directly separated and collected using a simple pipet, which eliminates the need for an external pump and does not require any electrical power. Some of the advantages of our plasma separator include higher capacity per unit area of the membrane than that afforded by other membrane-based devices, enabling a relatively large sample volume, which is important for greater downstream detection sensitivity, and self-terminating operation that protects against excessive hemolysis.

Plasma extracted with our plasma separator is appropriate for the molecular detection of target analytes contained in whole blood by spiking the blood with intact HIV virus and using the plasma in microfluidicbased nucleic acid amplification. The devices demonstrated high efficiency recovery and limit of detection of at least 350 viral copies per 1 mL of plasma. The current standard of care requires ability to detect over 1000 viral copies per mL of plasma. The novel, easy-to-use, plasma separator described herein can be used as a stand-alone separation device in resource-constrained settings, where laboratory facilities and trained personnel are in short supply.

What is claimed:

1. A plasma separator, comprising:
a chamber having one or more inner walls;
at least one membrane vertically or essentially vertically oriented within the chamber, the at least one membrane forming an inner cavity within the chamber,
a plasma collection space separated from the inner cavity by the at least one membrane; and
a plasma removal port,
wherein the plasma separator is configured to separate plasma from blood using gravitational sedimentation and filtration.

2. The plasma separator of claim 1, wherein the at least one membrane is hydrophilic.

3. The plasma separator of claim 1, wherein at least one of the one or more inner walls is superhydrophobic.

4. The plasma separator of claim 1 where at least one inner wall comprises one or more surface features.

5. The plasma separator of claim 4, wherein at least one of the surface features is a pillar.

6. The plasma separator of claim 4, wherein at least one of the surface features defines a groove.

7. The plasma separator of claim 4, wherein the feature supports the membrane.

8. The plasma separator of claim 1, wherein the chamber has a circular cross-section, rectangular cross-section, ellipsoidal cross-section, or triangular cross-section.

9. The plasma separator of claim 1, wherein the chamber has a cross-sectional dimension that varies within the chamber.

10. The plasma separator of claim 1, comprising:
a frame elongate along a central longitudinal axis, the frame having a top end and a bottom end spaced from the top end along the longitudinal axis, the frame defining the chamber that defines a void elongate along the central longitudinal axis,
a collection conduit;
a collection trench transverse to the central longitudinal axis and in fluid communication with the collection conduit, the frame further defining an outlet at a top end of the collection conduit; and
the at least one membrane comprises a pair of membranes disposed parallel to one another within the void, the pair of membranes together defining an inlet space to the void, the inlet space being defined between the pair of membranes.

11. The plasma separator of claim 10, wherein the void is partially defined by a left side of the frame and a right side of the frame opposite the left side, the frame further comprising a plurality of projections that extend from the left and right sides of the frame towards the pair of membranes.

12. The plasma separator of claim 11, wherein the left side and the right side of the frame are disposed between 1 mm to 1 cm apart.

13. The plasma separator of claim 12, wherein the left side and the right side of the frame are disposed approximately 5 mm apart.

14. The plasma separator of claim 11, wherein the projections extend approximately 100 μm from the left side and the right side, respectively.

15. The plasma separator of claim 10, wherein the void is partially defined by a left side of the frame and a right side of the frame opposite the left side, and each of the left and right sides define an aperture in fluid communication with the collection trench.

16. The plasma separator of claim 10, wherein the pair of membranes are configured to preferentially transport blood plasma from the inlet space across the membranes to the void.

17. The plasma separator of claim 1, comprising:
a frame defining a void and a conduit defining an outlet, wherein the at least one membrane is disposed within the void and supported by the frame, the at least one membrane at least partially defining an inlet.

18. The plasma separator of claim 17, wherein the at least one membrane comprises two membranes disposed approximately parallel to each other and the frame further comprises projections that extend into the void and partially support the two membranes.

19. The plasma separator of claim 17 wherein the at least one membrane forms one of the following shapes: a cube, a cuboid, a cylinder, a cone, a pyramid, a partial sphere, or a prism.

20. The plasma separator of claim 17 wherein the at least one membrane is configured to preferentially transport blood plasma across the membrane to the void.

21. The plasma separator of claim 17 further comprising a diagnostic device.

22. The plasma separator of claim 1, wherein the plasma separator is configured to separate plasma from blood via gravitational sedimentation that is in a direction that is parallel to the at least one membrane.

* * * * *

UNITED STATES PATENT AND TRADEMARK OFFICE
CERTIFICATE OF CORRECTION

PATENT NO. : 10,576,426 B2
APPLICATION NO. : 15/105887
DATED : March 3, 2020
INVENTOR(S) : Liu et al.

Page 1 of 2

It is certified that error appears in the above-identified patent and that said Letters Patent is hereby corrected as shown below:

On the Title Page

Item [56], References Cited, under heading OTHER PUBLICATIONS:

Replace "Balu et al., "Patterning of superhydrophobic paper to control the mobility of micro-liter drops from two-dimensional lab-on-paper applications", Lab on a Chip, Jan. 1, 2009, vol. 9, No. 21, p. 3066."
With --Balu et al., "Patterning of superhydrophobic paper to control the mobility of micro-liter drops from two-dimensional lab-on-paper applications", Lab on a Chip, November, 2009, vol. 9, No. 21, p. 3066-3075.--

Replace "Liu et al., "Membrane-based, sedimentation-assisted plasma separator for point-of-care applications", Analytical Chemistry, Oct. 5, 2013, vol. 85, pp. 10463, 10465-10467."
With --Liu et al., "Membrane-based, sedimentation-assisted plasma separator for point-of-care applications", Analytical Chemistry, Oct. 5, 2013, vol. 85, pp. 10463-10470.--

In the Specification

Under Heading BACKGROUND, Column no. 1, Line no. 55:
Replace "hemolysis. The HIV-laden plasma was then injected into a"
With --hemolysis. The HIV-laden plasma was then injected into an--

Under Heading SUMMARY, Column no. 4, Line no. 5:
Replace "defining a void and a conduit defining an outlet andat least"
With --defining a void and a conduit defining an outlet and at least--

Under Heading DETAILED DESCRIPTION OF ILLUSTRATIVE EMBODIMENTS, Column no. 11, Line no. 28:
Replace "using the plasma in microfluidicbased nucleic acid amplification."
With --using the plasma in microfluidic based nucleic acid amplification.--

Signed and Sealed this
Twenty-sixth Day of May, 2020

Andrei Iancu
*Director of the United States Patent and Trademark Office*

CERTIFICATE OF CORRECTION (continued)
U.S. Pat. No. 10,576,426 B2

In the Claims

Under what is claimed:

In Claim no. 4, Column no. 11, Line no. 53:
Replace "The plasma separator of claim 1 where at least one"
With --The plasma separator of claim 1, where at least one--

In Claim no. 19, Column no. 12:
Replace "The plasma separator of claim 17 wherein the at least"
With --The plasma separator of claim 17, wherein the at least--

In Claim no. 20, Column no. 12:
Replace "The plasma separator of claim 17 wherein the at least"
With --The plasma separator of claim 17, wherein the at least--

In Claim no. 21, Column no. 12:
Replace "The plasma separator of claim 17 further comprising"
With --The plasma separator of claim 17, further comprising--